United States Patent
Dyke et al.

(10) Patent No.: US 6,410,559 B2
(45) Date of Patent: Jun. 25, 2002

(54) HETEROCYCLIC COMPOUNDS AND THEIR THERAPEUTIC USE

(75) Inventors: Hazel Joan Dyke; John Gary Montana, both of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/822,071

(22) Filed: Mar. 30, 2001

Related U.S. Application Data

(62) Division of application No. 09/433,274, filed on Nov. 3, 1999, now Pat. No. 6,262,070.
(60) Provisional application No. 60/112,545, filed on Dec. 16, 1998.

(30) Foreign Application Priority Data

Nov. 4, 1998  (GB) .............................................. 9824160

(51) Int. Cl.$^7$ .............................................. A61K 31/47
(52) U.S. Cl. ........................................................ 514/311
(58) Field of Search ........................................ 514/311

(56) References Cited

U.S. PATENT DOCUMENTS

| 5,324,839 A | 6/1994 | Clemence et al. |
| 5,804,588 A | 9/1998 | Dyke et al. |

FOREIGN PATENT DOCUMENTS

| WO | 9744036 | 11/1997 |
| WO | 9748697 | 12/1997 |

OTHER PUBLICATIONS

Regan, J. et al. (1998) "2–substituted–4–methoxybenzimidazole–based PDE4 Inhibitors" *Bioorganic & Medicinal Chemistry Letters* 8(19):2737–2742.

Hulme, C. et al. (1998) "Orally Active Indole N–Oxide PDE4 Inhibitors" *Bioorganic & Medicinal Chemistry Letters* 8(21):3053–3058.

*Primary Examiner*—Zohreh Fay
(74) *Attorney, Agent, or Firm*—Saliwanchik, Lloyd & Saliwanchik

(57) ABSTRACT

N-oxides of formula (i)

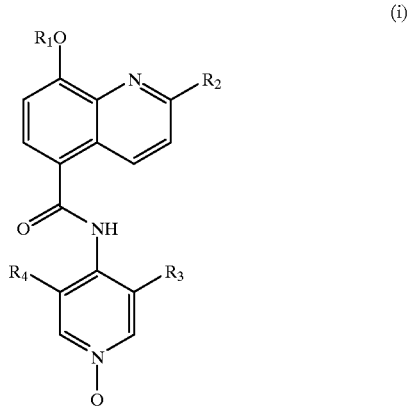

wherein $R_1$ is $CH_3$, $CH_2F$, $CHF_2$ or $CF_3$;
$R_2$ is $CH_3$ or $CF_3$;
$R_3$ is F, Cl, Br, CN or $CH_3$; and
$R_4$ is H, F, Cl, Br, CN or $CH_3$;

and pharmaceutically-acceptable salts thereof, are useful as therapeutic agents, e.g., for the treatment of inflammatory diseases.

6 Claims, 1 Drawing Sheet

HETEROCYCLIC COMPOUNDS AND THEIR THERAPEUTIC USE

CROSS-REFERENCE TO RELATED APPLICATIONS

This application is a divisional of application Ser. No. 09/433,274, filed Nov. 3, 1999, now U.S. Pat. No. 6,262,070 which claims priority from U.S. Ser. No. 60/112,545, filed Dec. 16, 1998, now abandoned.

FIELD OF THE INVENTION

The present invention relates to novel heterocyclic compounds and to their formulation and use as pharmaceuticals.

BACKGROUND OF THE INVENTION

EP-A-0498722 describes quinoline derivatives as angiotensin $A_2$ and endothelin inhibitors.

The modes of action of phosphodiesterases and also tumour necrosis factors (TNF), and the therapeutic utilities of inhibitors thereof, are described in WO-A-9744036 and U.S. Pat. No. 5804588, the contents of which are incorporated herein by reference. These publications specifically disclose quinoline carboxamides having such inhibitory activity.

SUMMARY OF THE INVENTION

This invention provides novel compounds having therapeutic utility, in particular for the treatment of disease states associated with proteins which mediate cellular activity, for example by inhibiting TNF and/or PDE IV. According to the invention, the compounds are of formula (i):

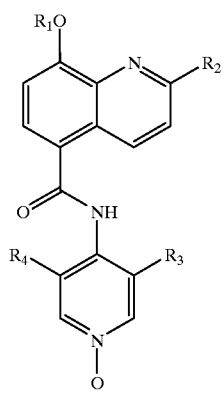

(i)

wherein
$R_1$ is $CH_3$, $CH_2F$, $CHF_2$ or $CF_3$;
$R_2$ is $CH_3$ or $CF_3$;
$R_3$ is F, Cl, Br, CN or $CH_3$; and
$R_4$ is H, F, Cl, Br, CN or $CH_3$;
or a pharmaceutically-acceptable salt thereof.

In summary, the compounds of the invention are N-oxides of the corresponding free bases which are disclosed, some specifically, in WO-A-9744036. The novel compounds have superior solubility, improved metabolic stability, and an improved pharmacokinetic profile. The compound of Example 8 is particularly preferred.

This invention provides also a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically-acceptable salt thereof.

DESCRIPTION OF THE INVENTION

Figure 1:
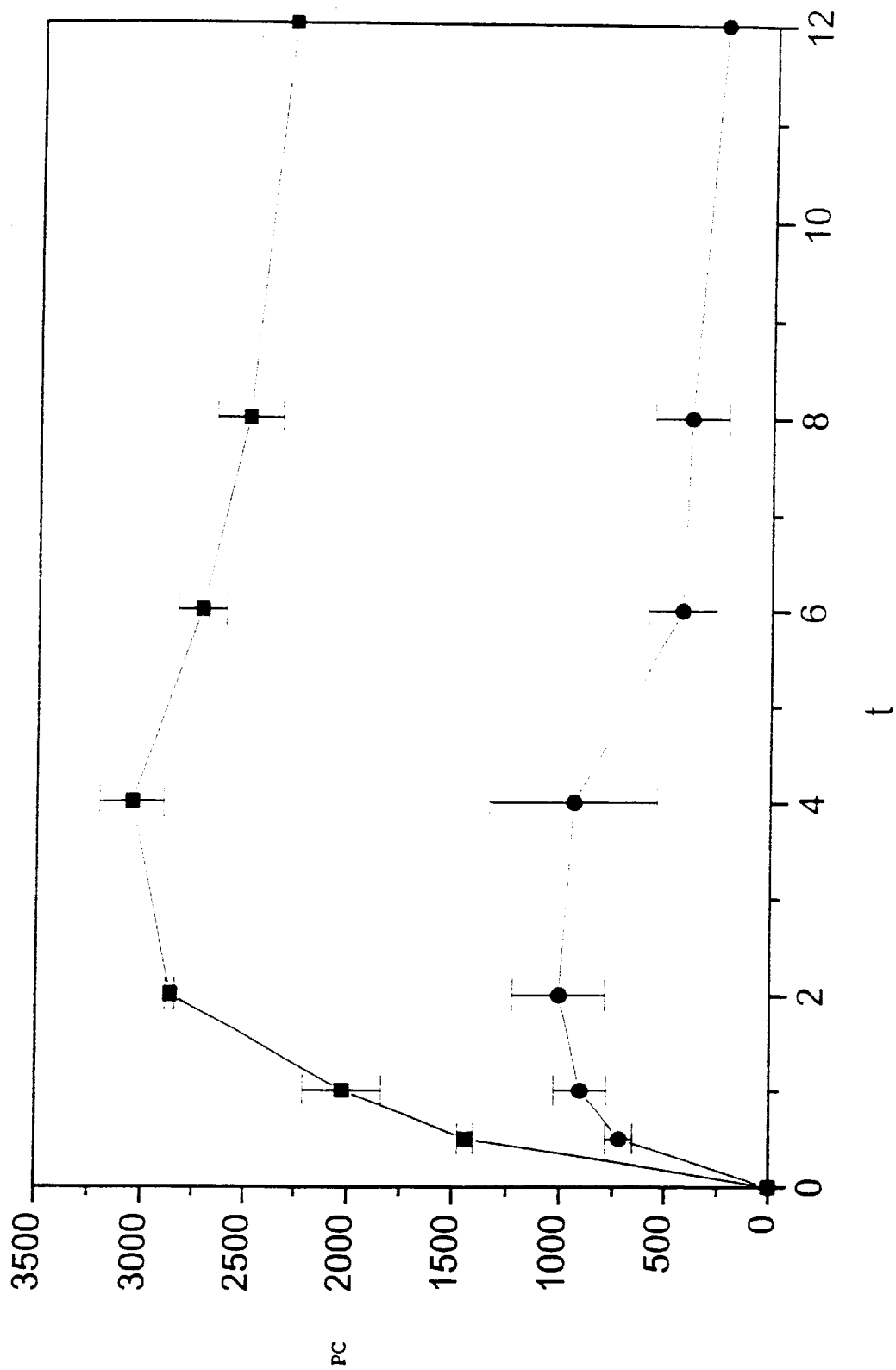
FIG. 1 is a graph showing pK data of the compound of Example 8 (indicated by ■) and the free base compound (indicated by ●) following oral dosing in a rat; PC (plasma concentration in ng/ml) is plotted against t (time in hours).

Certain of the compounds of formula (i) which contain a basic group form acid addition salts. Suitable acid addition salts include pharmaceutically-acceptable inorganic salts such as the sulphate, nitrate, phosphate, borate, hydrochloride and hydrobromide, and pharmaceutically-acceptable organic acid addition salts such as acetate, tartrate, maleate, citrate, succinate, benzoate, ascorbate, methanesulphate, α-ketoglutarate, α-glycerophosphate and glucose-1-phosphate. The pharmaceutically-acceptable salts of the compounds of formula (i) are prepared using conventional procedures.

Compounds of the invention may be prepared by N-oxidation of the corresponding free base. The free bases are known, or can be prepared by the processes disclosed in WO-A-9744036. For example, a compound of formula (i) may be prepared by treating the free base with peracetic acid in acetic acid in an appropriate solvent such as chloroform, or with hydrogen peroxide in acetic acid.

The invention includes the prevention and treatment of TNF mediated disease or disease states, by which is meant any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biological responses and binds to the same cellular receptor, both TNF-α and TNF-β are inhibited by compounds of the present invention and thus are herein referred to collectively as "TNF" unless specifically delineated otherwise.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (i) or a pharmaceutically-acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically-acceptable form. By pharmaceutically-acceptable form is meant, inter alia, a pharmaceutically-acceptable level of purity excluding normal pharmaceutical additives such as diluents and carriers, and including no material considered toxic at normal dosage levels. A pharmaceutically-acceptable level of purity will generally be at least 50% excluding normal pharmaceutical additives, preferably 75%, more preferably 90% and still more preferably 95%. When used herein the term "pharmaceutically-acceptable" encompasses materials suitable for both human and veterinary use.

A compound of formula (i) or where appropriate a pharmaceutically-acceptable salt thereof and/or a pharmaceutically-acceptable solvate thereof, may be administered per se or, preferably, as a pharmaceutical composition also comprising a pharmaceutically-acceptable carrier.

Accordingly, the present invention provides a pharmaceutical composition comprising a compound of formula (i) or where appropriate a pharmaceutically-acceptable salt thereof and/or a pharmaceutically-acceptable solvate thereof, and a pharmaceutically-acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose. Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically-acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia, non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 $\mu$m, such as from 0.1 to 50 $\mu$m, preferably less than 10 $\mu$m, for example from 1 to 10 $\mu$m, 1 to 5 $\mu$m or from 2 to 5 $\mu$m. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions, the compound can be dissolved in water for injection and filter-sterilised before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically-acceptable salt thereof and/or a pharmaceutically-acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically-acceptable salt thereof, are conventional formulations well known in the art, for example, as described in standard text books such as Harry's Cosmeticology published by Leonard Hill Books, Remington's Pharmaceutical Sciences, and the British and U.S. Pharmacopoeias.

Suitably, the compound of formula (i), or if appropriate a pharmaceutically-acceptable salt thereof, will compromise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10 mg, for example 0.5, 1, 2, 3, 4 or 5 mg; and such unit doses may be administered more than once a day, for example 2, 3, 4, 5 or 6 times a day, but preferably 1 or 2 times per day, so that the total daily dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

Assay Methods

The assays used to confirm the phosphodiesterase IV inhibitory activity of compounds of formula (I) are standard assay procedures as disclosed by Schilling et al, Anal. Biochem. 216:154 (1994), Thompson and Strada, Adv. Cycl. Nucl. Res. 8:119 (1979) and Gristwood and Owen, Br. J. Pharmacol. 87:91P (1986).

Compounds of formula (i) have exhibited activity at levels consistent with those believed to be useful in treating phosphodiesterase IV related disease states in those assays.

The ability of compounds of formula (i) to inhibit TNF production in human peripheral blood mononuclear cells (PMBC's) is measured as follows. PMBC's are prepared from freshly taken blood or "Buffy coats" by standard procedures. Cells are plated out in RPMI1640+1% foetal calf serum in the presence and absence of inhibitors. LPS (Lipopolysaccharide (endotoxin); 100 ng/ml) is added and cultures are incubated for 22 h at 37° C. in an atmosphere of 95% air/5% $CO_2$. Supernatants are tested for TNFα by ELISA (Enzyme linked immunosorbent assay) using commercially available kits.

Abbreviations

Activity in a guinea pig lung model is measured using the procedures described by Mauser et al, Am. Rev. Respir. Dis. 148:1623 (1993), and Am. J. Respir. Crit. Care Med. 152:467 (1995).

The pharmacokinetic profile of the compounds of the invention is determined in rats cannulated in the right carotid artery for blood collection. For iv dosing, the compound is prepared in a suitable formulation, for example 10% v/v DMSO, 50% v/v PEG 400 in water, and dosing is carried out by cannulation of the left jugular vein. Samples are collected at 5 min, 0.5, 1, 2, 4, 6 and 8 hours post-dosing. For oral dosing, the compound is prepared in a suitable formulation such as 0.4% w/v methylcellulose in water. Samples are collected at 0.5, 1, 2, 4, 6 and 8 hours post-dosing. In some cases, samples are also collected at 12 hours post-dosing. Plasma is obtained by centrifugation of the each blood sample and drug concentration is then determined using standard methods, such as liquid chromatography-mass spectrometry following protein precipitation.

Results are tabulated below, and are also shown in the accompanying drawing. The drawing is a graph of PK data following oral dosing in the rat; PC (plasma concentration; ng/ml) is plotted against t (time; hours). ■ represents the compound of Example 8, and ● the free base. The superiority of the novel compound is evident.

|  | Example 8 | Free base |
|---|---|---|
| Dose (iv) (mg/kg) | 1 | 1 |
| Dose (po) (mg/kg) | 3 | 3 |
| Cmax (po) (ng/ml) | 3054 | 1008 |
| $AUC_{0-last}$ (po) (ng · h/ml) | 30169 | 6860 |
| $t_{1/2}$ (po) (h) | 20 | 4.5 |

The solubility of the compound of Example 8, in water at pH 7, was 0.2 mg/ml. The solubility of the corresponding free base, under the same conditions, was 0.002 mg/ml. Other exemplified compounds exhibit desirable solubility.

The following Examples illustrate the invention.

Intermediate 1

2-Trifluoromethylquinolin-8-ol

A solution of 8-methoxy-2-trifluoromethylquinoline (10.0 g) in 48% hydrobromic acid (40 ml) was stirred at reflux overnight. The reaction mixture was poured into water (200 ml) and the pH adjusted to 12.5 using 46–48% sodium hydroxide solution. After extraction with dichloromethane (2×25ml) the aqueous layer was acidified to pH 5.3 by the addition of 37% hydrochloric acid solution. The mixture was then extracted using dichloromethane (2×100 ml) and the combined organic extracts washed with water, dried over sodium sulfate, filtered and the solvent removed in vacuo to give the product (9.3 g) as a white solid.

M.S. [M+H]214

Intermediate 2

8-(Tert-butyldimethylsilanyloxy)-2-trifluoromethylquinoline

A solution of 2-trifluoromethylquinolin-8-ol (11.5 g), tert-butyldimethylsilyl chloride (8.9 g) and triethylamine (6.5 g) in dichloromethane (60 ml) was stirred overnight at room temperature. The reaction mixture was washed with water (2×50 ml), dried over sodium sulfate, filtered and the solvent removed in vacuo to give the product (17.9 g) as a white solid.
M.S. [M+H]328

The following Intermediate was prepared by a similar procedure.
Intermediate 3

8-(Tert-butyldimethylsilanyloxy)-2-methylquinoline

Prepared from 8-hydroxyquinaldine (10 g) to give the product (17 g) as an orange oil.
TLC $R_f$ 0.90 (10% methanol in ethyl acetate)
Intermediate 4

5-Bromo-8-(tert-butyldimethylsilanyloxy)-2-trifluoromethylquinoline

A solution of 8-(tert-butyldimethylsilanyloxy)-2-trifluoromethylquinoline (17.5 g) in dichloromethane (100 ml) was treated with N-bromosuccinimide (10.5 g) at 15° C. The mixture was stirred at 20° C. for 25 minutes, washed with 1% sodium sulfite solution (100 ml), and water (50 ml). The organic layer was separated, dried over magnesium sulfate, filtered and the solvent removed in vacuo to give the product (21.4 g) as a dark oil.
M.S. [M+H]406

The following Intermediate was prepared by a similar procedure.
Intermediate 5

5-Bromo-8-(tert-butyldimethylsilanyloxy)-2-methylquinoline

Prepared from 8-(tert-butyldimethylsilanyloxy)-2-methylquinoline (0.63 g) to give the product (0.66 g) as a yellow oil.
TLC $R_f$ 0.90 (dichloromethane)
Intermediate 6

5-Bromo-2-trifluoromethylquinolin-8-ol

A solution of 5-bromo-8-(tert-butyldimethylsilanyloxy)-2-trifluoromethylquinoline (21 g) in methanol (150 ml) was treated with 37% hydrochloric acid solution (5 ml) and water (5 ml). The mixture was stirred for 12h at room temperature and at 45° C. for 2 h. The methanol was removed in vacuo and the residue partitioned between 10% sodium hydroxide solution (100 ml) and dichloromethane (50 ml). The aqueous layer was neutralised with 37% hydrochloric acid solution to pH 7.2 and extracted with dichloromethane (4×50 ml). The combined organic extracts were dried over magnesium sulfate, filtered and the solvent removed in vacuo to give the product (12 g) as a cream solid.
M.S. [M+]292
Intermediate 7

5-Bromo-2-methylquinolin-8-ol

A solution of 5-bromo-8-(tert-butyldimethylsilanyloxy)-2-methylquinoline (16.3 g) in tetrahydrofuran (500 ml) was treated dropwise with a solution of tetrabutylammonium fluoride (1.0M in tetrahydrofuran, 54 ml). The mixture was stirred for 10 minutes, diluted with dichloromethane (750 ml) and washed with water (3×250 ml). The organic solution was dried over magnesium sulphate, filtered and the solvent removed in vacuo to give an orange oil. Recrystallisation from aqueous methanol gave the product (7.65 g) as a white solid.

TLC $R_f$ 0.58 (10% methanol in dichloromethane).
Intermediate 8

5-Bromo-8-difluoromethoxy-2-trifluoromethylquinoline

To a stirred solution of 5-bromo-2-trifluoromethylquinolin-8-ol (12.0 g) in dioxane (120 ml) was added 47% sodium hydroxide solution (12 ml). The mixture was heated to 78° C. and chlorodifluoromethane (7.4 g) was bubbled through the reaction over 3 h. On cooling, the mixture was diluted with water (80 ml) and the solvent removed in vacuo. The resulting slurry was filtered and the filter cake washed with dichloromethane (50 ml) then water (50 ml). The organic layer was separated and the aqueous layer extracted with dichloromethane (50 ml). The combined organic extracts were washed with 0.5% sodium hydroxide solution (100 ml), dried over magnesium sulfate, filtered and the solvent removed in vacuo. The residue was taken up in tert-butyl methyl ether (100 ml), the cloudy solution filtered and the solvent removed in vacuo to give the product (11.7 g) as an off white solid.
M.S [M+H]342

The following Intermediate was prepared by a similar procedure.
Intermediate 9

5-Bromo-8-difluoromethoxy-2-methylquinoline

Prepared from 5-bromo-2-methylquinolin-8-ol (1.0 g) to give a brown solid. Purification by recrystallisation from methanol gave the product (0.96 g) as an off white solid.
TLC $R_f$ 0.86 (50% ethyl acetate in hexane)
Intermediate 10

8-Difluoromethoxy-2-trifluoromethylquinoline-5-carboxylic acid

A mixture of 5-bromo-8-difluoromethoxy-2-trifluoromethylquinoline (6.0 g), triphenylphosphine (0.3 g), bis(triphenylphosphine)palladium (II) chloride (0.15 g), 47% sodium hydroxide solution (4.5 g) and water (12 ml) in tetrahydrofuran (50 ml) was purged with carbon monoxide gas in a Parr pressure reactor at 7 bar. This was heated to 100° C. for 24 h. After cooling and venting the reaction mixture was partitioned between sodium hydroxide solution (1.5 g in 50 ml) and tert-butyl methyl ether (100 ml). The organic solution was extracted with sodium hydroxide solution (2×5 g in 50 ml). The combined aqueous extracts were stirred with activated charcoal (1.5 g) for 15 minutes and then filtered. The filtrate was acidified to pH 4 using 37% hydrochloric acid solution and the resultant cream precipitate isolated by filtration and washed with water (20 ml). The crude product was purified by recrystallisation from toluene to give the product (1.8 g) as a cream solid.
M.S [M+H]308

The following Intermediate was prepared by a similar procedure.
Intermediate 11

8-Difluoromethoxy-2-methylquinoline-5-carboxylic acid

Prepared from 5-bromo-8-difluoromethoxy-2-methylquinoline (5.72 g) to give the product (2.88 g) as a brown solid.
TLC $R_f$ 0.60 (10% methanol in dichloromethane)
Intermediate 12

8-Difluoromethoxy-2-trifluoromethylquinoline-5-carboxylic acid 4-nitrophenyl ester A solution of 8-difluoromethoxy-2-trifluoromethylquinoline-5-carboxylic acid (0.5 g) in dichloromethane (50 ml) was treated with 4-nitrophenol (0.25 g), 4-dimethylaminopyridine (catalytic) and 1-(3-dimethylaminopropyl)-3-ethylcarbodiimide (0.3 5 g) and the mixture was stirred at room temperature for 12 h. The reaction was washed with water (50 ml), dried over sodium sulphate, filtered and the solvent removed in vacuo. The residue was purified by column chromatography on silica eluting with dichloromethane to give the product (0.47 g) as a cream solid.
TLC $R_f$ 0.75 (5% ethyl acetate in dichloromethane).
The following Intermediates were prepared by a similar procedure.
Intermediate 13

8-Difluoromethoxy-2-methylquinoline-5-carboxylic acid 4-nitrophenyl ester

Prepared from 8-difluoromethoxy-2-methylquinoline-5-carboxylic acid (0.50 g). Purification by column chromatography on silica eluting with 50% ethyl acetate in hexane gave the product (0.63 g) as yellow solid.
TLC $R_f$ 0.73 (10% methanol in dichloromethane)
Intermediate 14

8-Methoxy-2-trifluoromethylquinoline-5-carboxylic acid 4-nitrophenyl ester

Prepared from 8-methoxy-2-trifluoromethylquinoline-5-carboxylic acid (0.60 g) to give the title compound (0.75 g) as a yellow solid.
TLC $R_f$ 0.64 (50% ethyl acetate in hexane)
Intermediate 15

8-Difluoromethoxy-2-methylquinoline-5-carboxylic acid (3-chloropyridin-4-yl)amide To a stirred solution of 4-amino-3-chloropyridine (136mg) in N,N-dimethylformamide (2 ml) under an atmosphere of nitrogen was added sodium hydride (60% dispersion in oil, 42 mg). The reaction mixture was stirred at room temperature for 1 h. 8-Difluoromethoxy-2-methylquinoline-5-carboxylic acid 4-nitrophenyl ester (200 mg) was then added and stirring continued for 18 h. The solvent was removed in vacuo and the resulting residue purified by column chromatography on silica eluting with 50% ethyl acetate in hexane to give the product (155 mg) as a white solid.
TLC $R_f$ 0.3 (50% ethyl acetate in hexane)
The following Intermediates were prepared by a similar procedure.
Intermediate 16

8-Difluoromethoxy-2-methylquinoline-5-carboxylic acid (3-methylpyridin-4-yl)amide Prepared from 8-difluoromethoxy-2-methylquinoline-4-carboxylic acid 4-nitrophenyl ester (500 mg) and 4-amino-3-methylpyridine (170 mg). Purification by column chromatography on silica eluting with 10% methanol in dichloromethane gave the product (200 mg) as a pale yellow solid.
TLC $R_f$ 0.55 (10% methanol in ethyl acetate)
Intermediate 17

8-Difluoromethoxy-2-trifluoromethylquinoline-5-carboxylic acid (3-chloropyridin-4-yl)amide Prepared from 8-difluoromethoxy-2-trifluoromethylquinoline-5-carboxylic acid 4-nitrophenyl ester (466 mg) and 4-amino-3-chloropyridine (283 mg). Purification by column chromatography on silica eluting with 15% ethyl acetate in dichloromethane gave the product (297 mg) as a white solid.
TLC $R_f$ 0.26 (15% ethyl acetate in dichloromethane)
Intermediate 18

8-Difluoromethoxy-2-trifluoromethylquinoline-5-carboxylic acid (3,5-dichloropyridin-4-yl)amide Prepared from 8-difluoromethoxy-2-trifluoromethylquinoline-5-carboxylic acid 4-nitrophenyl ester (480 mg) and 4-amino-3,5-dichloropyridine (360 mg). Purification by column chromatography on silica eluting with 20% ethyl acetate in hexane gave the product (424 mg) as a white solid.
TLC $R_f$ 0.42 (20% ethyl acetate in hexane)
Intermediate 19

8-Difluoromethoxy-2-trifluoromethylquinoline-5-carboxylic acid (3,5-difluoropyridin-4-yl)amide Prepared from 8-difluoromethoxy-2-trifluoromethylquinoline-5-carboxylic acid 4-nitrophenyl ester (390 mg) and 4-amino-3,5-difluoropyridine (120 mg). Purification by column chromatography on silica eluting with 10% ethyl acetate in dichloromethane gave the product (180 mg) as a white solid.
TLC $R_f$ 0.27 (15% ethyl acetate in dichloromethane)
Intermediate 20

8-Methoxy-2-trifluoromethylquinoline-5-carboxylic acid (3,5-difluoropyridin-4-yl)amide Prepared from 8-methoxy-2-trifluoromethylquinoline-5-carboxylic acid 4-nitrophenyl ester (425 mg) and 4-amino-3,5-difluoropyridine (282 mg). Purification by column chromatography on silica eluting with 5% methanol in dichloromethane gave the product (162 mg) as a white solid.
TLC $R_f$ 0.34 (5% methanol in dichloromethane)
Intermediate 21

8-Methoxy-2-trifluoromethylquinoline5-carboxylic acid (3-chloropyridin-4-yl)amide To a stirred solution of 4-amino-3-chloropyridine (124 mg) in N,N-dimethylformamide (5 ml) under an atmosphere of nitrogen was added sodium hydride (60% dispersion in oil, 52 mg). The reaction mixture was stirred at room temperature for 1 h. 8-Methoxy-2-trifluoromethylquinoline-4-carbonyl chloride (360 mg) was then added and stirring continued for 18 h. The solvent was removed in vacuo and the resulting residue partitioned between ethyl acetate (2×50 ml) and water (5 ml). The organic layer was separated, dried over magnesium sulphate, filtered and the solvent removed in vacuo. Purification by column chromatography on silica eluting with ethyl acetate gave the product (330 mg) as a pale pink solid.
TLC $R_f$ 0.41 (ethyl acetate)
mp 192–194° C.
The following Intermediate was prepared by a similar procedure.
Intermediate 22

8-Methoxy-2-trifluoromethylquinoline-5-carboxylic acid (3-methylpyridin-4-yl)amide Prepared from 8-methoxy-2-trifluoromethylquinoline-4-carbonyl chloride (430 mg) and 4-amino-3-methylpyridine (170 mg). Purification by column chromatography eluting with 10% methanol in ethyl acetate gave the product (160 mg) as a white solid.

TLC $R_f$ 0.29 (10% methanol in ethyl acetate)
Intermediate 23

8-Difluoromethoxy-2-trifluoromethylquinoline-5-carboxylic acid (3-methylpyridin-4-yl)amide A solution of 8-difluoromethoxy-2-trifluoromethylquinoline-4-carboxylic acid (0.50 g) in dichloromethane (30 ml) was stirred at room temperature under an atmosphere of nitrogen. Oxalyl chloride (0.28 ml) was added followed by N,N-dimethylformamide (1 drop) and stirring continued overnight. The solvent was removed in vacuo to give 8-difluoromethoxy-2-trifluoromethylquinoline-4-carbonyl chloride (650 mg) as an off white solid.

To a stirred solution of 8-difluoromethoxy-2-trifluoromethylquinoline-4-carbonyl chloride (650 mg) in dichloromethane (40 ml) under an atmosphere of nitrogen was added triethylamine (0.68 ml) and 4-amino-3-methylpyridine (352 mg). The reaction mixture was stirred for 18 h. The solvent was removed in vacuo and the resulting residue purified by column chromatography on silica eluting with 5% methanol in dichloromethane to give the product (563 mg) as a pale white solid.
TLC $R_f$ 0.53 (10% methanol in dichloromethane)
The following Intermediate was prepared by a similar procedure
Intermediate 24

8-Methoxy-2-trifluoromethylquinoline-5-carboxylic acid (3,5-dimethylpyridin-4-yl)amide Prepared from 8-methoxy-2-trifluoromethylquinoline4-carbonyl chloride (500 mg) and 4-amino-3,5-dimethylpyridine (210 mg). Purification by trituration with acetone and ether gave the product (82 mg) as a pale yellow solid.
TLC $R_f$ 0.42 (10% methanol in dichloromethane with 1% ammonium hydroxide)

EXAMPLE 1

8-Difluoromethoxy-2-methylquinoline-5-carboxylic acid (3-chloro-1-oxypyridin-4-yl)amide Peracetic acid (36–40% in acetic acid, 0.1 ml) was added to a solution of 8-difluoromethoxy-2-methylquinoline-5-carboxylic acid (3-chloropyridin-4-yl)amide (50 mg) in chloroform (10 ml) at room temperature. After stirring overnight the reaction was diluted with dichloromethane (20 ml) and washed with water (20 ml). The organic phase was dried over magnesium sulfate and the solvent removed it in vacuo to give a white solid. Purification by column chromatography eluting with 10% methanol in ethyl acetate gave the product (25 mg) as a white solid.
TLC $R_f$ 0.2 (10% methanol in ethyl acetate)
mp 244° C. (dec.)
The following Examples were prepared by a similar procedure.

EXAMPLE 2

8-Difluoromethoxy-2-trifluoromethylquinoline-5-carboxylic acid (3-chloro-1-oxypyridin-4-yl)amide Prepared from 8-difluoromethoxy-2-trifluoromethylquinoline-5-carboxylic acid (3-chloropyridin-4-yl)amide (261 mg) to give the product (223 mg) as a cream solid.
TLC $R_f$ 0.4 (ethyl acetate)
mp 212–213° C.

EXAMPLE 3

8-Methoxy-2-trifluoromethylquinoline5-carboxylic acid (3-chloro-1-oxypyridin-4-yl)amide Prepared from 8-methoxy-2-trifluoromethylquinoline-5-carboxylic acid (3-chloropyridin-4-yl)amide (50 mg) to give the product (25 mg) as an off white solid.
TLC $R_f$ 0.7 (10% methanol in ethyl acetate)
mp 261.5–262.5° C.

EXAMPLE 4

8-Methoxy-2-trifluoromethylquinoline-5-carboxylic acid (3,5-difluoro-1-oxypyridin-4-yl)amide Prepared from 8-methoxy-2-trifluoromethylquinoline-5-carboxylic acid (3,5-difluoropyridin-4-yl)amide (120 mg) with stirring at room temperature for two weeks. Excess peracetic acid (4×0.5 ml) was added over this period. Purification by column chromatography eluting with 5-10% methanol in dichloromethane gave the product (28 mg) as a yellow solid.
TLC $R_f$ 0.09 (5% methanol in dichloromethane)
mp 268–269° C. (dec.)

EXAMPLE 5

8-Difluoromethoxy-2-trifluoromethylquinoline-5-carboxylic acid (3,5-difluoro-1-oxypyridin-4-yl)amide Prepared from 8-difluoromethoxy-2-trifluoromethylquinoline-5-carboxylic acid (3,5-difluoropyridin-4-yl)amide (160 mg) with stirring at room temperature for two weeks. Excess peracetic acid (3×0.1 ml) was added over this period. Purification by column chromatography eluting with 15% ethyl acetate in dichloromethane increasing to 10% methanol in dichloromethane gave the product (120 mg) as a yellow solid.
TLC $R_f$ 0.69 (2% methanol in dichloromethane)
mp 219–220° C.

EXAMPLE 6

8-Difluoromethoxy-2-trifluoromethylquinoline-5-carboxylic acid (3-methyl-1-oxypyridin-4-yl)amide Prepared from 8-difluoromethoxy-2-trifluoromethylquinoline-5-carboxylic acid (3-methylpyridin-4-yl)amide (316 mg) stirred in the presence of peracetic acid (2×0.18 ml) for two days. Purification by column chromatography eluting with 10% methanol in dichloromethane gave the product (267 mg) as a white solid.
TLC $R_f$ 0.25 (10% methanol in dichloromethane)
mp 210–212° C.

EXAMPLE 7

8-Methoxy-2-trifluoromethylquinoline5-carboxylic acid (3,5-dimethyl-1-oxypyridin-4-yl)amide Prepared from 8-methoxy-2-trifluoromethylquinoline-5-carboxylic acid (3,5-dimethylpyridin-4-yl)amide (56 mg) stirred in the presence of peracetic acid (2×0.05 ml) for two days. Purification by column chromatography eluting with 1% ammonium hydroxide/10% methanol in dichloromethane gave the product (37 mg) as a white solid.

TLC $R_f$ 0.22 (1% ammonium hydroxide/10% methanol in dichloromethane)
mp 237–239° C.

EXAMPLE 8

8-Methoxy-2-trifluoromethylquinoline-5-carboxylic acid (3,5-dichloro-1-oxypyridin-4-yl)amide 8-Methoxy-2-trifluoromethylquinoline-5-carboxylic acid (3,5-dichloropyridin4-yl)amide (200 mg) was stirred in the presence of peracetic acid (36-40% in acetic acid, 0.1 ml) in chloroform at 50° C. for 5 days. Additional peracetic acid (0.1 ml) was added and the reaction heated for a further 2 days. Purification by column chromatography eluting with 10% methanol in ethyl acetate gave the product (123 mg) as a white solid.
TLC $R_f$ 0.17 (10% methanol in ethyl acetate)
mp 280–281 ° C.

EXAMPLE 9

8-Difluoromethoxy-2-trifluoromethylquinoline-5-carboxylic acid (3,5-dichloro-1-oxypyridin-4-yl) amide Prepared from 8-difluoromethoxy-2-trifluoromethylquinoline-5-carboxylic acid (3,5-dichloropyridin-4-yl)amide (415 mg) in a similar manner to 8-methoxy-2-trifluoromethyl-quinoline-5-carboxylic acid (3,5-dichloro-1-oxy-pyridin4-yl)-amide. Purification by column chromatography eluting with 1% ammonium hydroxide/10% methanol in dichloromethane afforded the title compound as a cream solid (360 mg).
TLC $R_f$ 0.5 (1% ammonium hydroxide/10% methanol in dichloromethane)
mp 244–245° C.

EXAMPLE 10

8-Difluoromethoxy-2-methylquinoline-5-carboxylic acid (3-methyl-1-oxypyridin-4-yl)amide Sodium hydride (60% dispersion in oil, 0.11 g) was added to a stirred solution of 3-methyl-1-oxypyridin-4-ylamine (0.2 g) in N,N-dimethylformamide (10 ml) under nitrogen at room temperature in the presence of molecular sieves. After stirring for one hour 8-difluoromethoxy-2-methylquinoline-5-carboxylic acid 4-nitrophenyl ester was added and the reaction stirred overnight. The solvent was removed in vacuo and the residue partitioned between ethyl acetate (50 ml) and water (2×50 ml). The organic phase was dried over magnesium sulfate and concentrated in vacuo. The residue was washed with a little ethyl acetate and dried to give the product (50 mg) as a pale yellow solid.
TLC $R_f$ 0.27 (1% triethylamine/20% methanol in dichloromethane)
mp 231.5–233.5° C.

EXAMPLE 11

8-Methoxy-2-trifluoromethylquinoline-5-carboxylic acid (3-methyl-1-oxypyridin-4-yl)amide Triethylamine (0.55 ml) and 4-dimethylaminopyridine (catalytic) were added to a stirred suspension of 3-methyl-1-oxypyridin-4-ylamine (0.23 g) in dichloromethane (40 ml) under nitrogen at room temperature. 8-Methoxy-2-trifluoromethylquinoline-5-carbonyl chloride, hydrochloride salt (0.6 g) was added and the reaction stirred overnight. The solvent was removed in vacuo and the residue partitioned between ethyl acetate (50 ml) and water (3×50 ml). The precipitate in the organic phase was filtered off and dried in vacuo at 45° C. to give the product (0.2 g) as a white solid.
TLC $R_f$ 0.12 (ethyl acetate)
mp 249.5–250.5 ° C.

We claim:

1. A method for the treatment of a disease state that is capable of being modulated by inhibition of phosphodiesterase IV or Tumour Necrosis Factor, or that is a pathological condition associated with a function of phosphodiesterase IV, eosinophil accumulation or a function of the eosinophil, wherein the disease state is an inflammatory disease or an autoimmune disease, said method comprising administering to a person or animal an effective amount of the compound of formula (i)

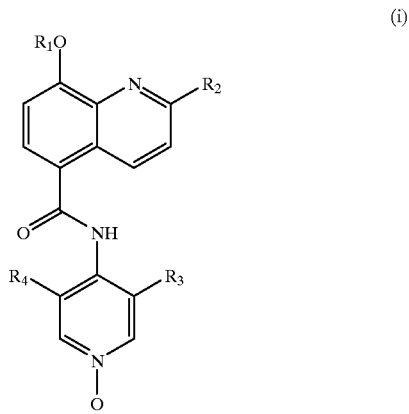

wherein
$R_1$ is $CH_3$, $CH_2F$, $CHF_2$ or $CF_3$;
$R_2$ is $CH_3$ or $CF_3$;
$R_3$ is F, Cl, Br, CN or $CH_3$; and
$R_4$ is H, F, Cl, Br, CN or $CH_3$;
or a pharmaceutically-acceptable salt thereof.

2. The method of claim 1, wherein the disease state is selected from the group consisting of chronic bronchitis, chronic pulmonary inflammatory disease, atopic dermatitis, allergic rhinitis, psoriasis, arthritis, rheumatoid arthritis, joint inflammation, ulcerative colitis, Crohn's disease, atopic eczema, stroke, bone resorption disease, multiple sclerosis and inflammatory bowel disease.

3. The method of claim 1, wherein the disease state is chronic bronchitis.

4. The method of claim 1, wherein the compound is 8-methoxy-2-trifluoromethylquinoline-5-carboxylic acid (3,5-dichloro-1-oxypyridin-4-yl)amide.

5. The method of claim 2, wherein the compound is 8-methoxy-2-trifluoromethylquinoline-5-carboxylic acid (3,5-dichloro-1-oxypyridin-4-yl)amide.

6. The method of claim 3, wherein the compound is 8-methoxy-2-trifluoromethylquinoline-5-carboxylic acid (3,5-dichloro-1-oxypyridin-4-yl)amide.

* * * * *